United States Patent [19]

Priddy et al.

[11] 4,389,517

[45] Jun. 21, 1983

[54] HYDROGENATION OF PHENYLACETYLENE PRIOR TO STYRENE POLYMERIZATION

[75] Inventors: Duane B. Priddy; James M. Roe, both of Midland, Mich.

[73] Assignee: The Dow Chemical Company, Midland, Mich.

[21] Appl. No.: 364,958

[22] Filed: Apr. 2, 1982

[51] Int. Cl.³ .................. C08F 4/48; C08F 112/08
[52] U.S. Cl. ........................... 526/64; 526/76; 526/346

[58] Field of Search ................... 526/76, 64

[56] References Cited

U.S. PATENT DOCUMENTS 2,813,089  11/1957  Twaddle et al. ............ 526/76

Primary Examiner—Stanford M. Levin
Attorney, Agent, or Firm—R. B. Ingraham

[57] ABSTRACT

A polystyrene is prepared from a $C_8$ cracker stream by first hydrogenating phenylacetylene to styrene and subsequently anionically polymerizing the styrene.

4 Claims, No Drawings

HYDROGENATION OF PHENYLACETYLENE PRIOR TO STYRENE POLYMERIZATION

For many years polystyrene has been a desired item of commerce and a number of companies compete for their share of the market. The polystyrenes commercially available range from relatively low molecular weight brittle materials used in formulation of paints, lacquers and the like, to higher molecular weight products suitable for moldings. The polystyrene market is highly competitive, particularly in the field of molding and extrusion resins. Therefore, it is desirable that a process used to prepare such polymers should provide the desired end results at minimal cost in time and energy, processing equipment and the like. Styrene monomer has been prepared by ethylation of benzene to provide ethylbenzene which is subsequently dehydrogenated to styrene and the product subsequently purified to provide a polymerization grade styrene; that is, a styrene of sufficient purity that it would polymerize readily to provide a generally water-white polymer. One attempt at providing a more economical route to polystyrene is set forth in U.S. Pat. No. 2,813,089, issued to W. W. Twaddle et al. In the Twaddle et al. patent, a process is disclosed wherein aromatic $C_8$ cut from the cracking of petroleum provides a mixture consisting primarily of xylenes and ethylbenzene. This stream is subsequently dehydrogenated to provide a mixture of styrene and three isomers of xylene. The stream is then treated with metallic sodium to cause polymerization of the styrene; the stream is filtered, devolatilized and the polystyrene recovered.

It is an object of this invention to provide an improved process for the preparation of polystyrene from a petroleum byproduct stream.

It is also an object of this invention to provide a method for the preparation of styrene polymers from a petroleum byproduct stream using minimal equipment.

It is a further object of this invention to prepare styrene polymers of molding grade quantity in a direct manner from a petroleum byproduct stream.

These objects and other advantages in accordance with the present invention are achieved in a process for the preparation of styrene polymers from a petroleum byproduct stream by providing a byproduct stream from the cracking of petroleum products, the stream containing primarily compounds containing 8 carbons and of an aromatic nature, the stream comprising 30 to 60 parts by weight styrene, 40 to 70 parts by weight of mixed isomers of xylene and 0.5 to 2 parts by weight of phenylacetylene, hydrogenating at least a major portion of the phenylacetylene in the stream to styrene, passing the hydrogenated stream to a continuously stirred tank reactor and initiating polymerization of the styrene in the stream with an organolithium initiator whereby at least 99 percent of the styrene initially present in the stream is converted to polymer, discharging the stream from the reactor and recovering styrene polymer therefrom.

Cracker streams suitable for the practice of the present invention are generally those obtained from the $C_8$ cut in the cracking of petroleum to prepare gasoline. Generally, the only component which is harmful to the polymerization of the styrene in such a stream is phenylacetylene which is believed to act as a chain transfer agent and results in polymers that have a molecular weight which is too low to be useful in the molding and extrusion fields. The phenylacetylene is readily removed from such cracker streams by hydrogenation. Phenylacetylene is more readily hydrogenated than is styrene and if the hydrogenation is carefully done and preferably monitored by a gas chromatograph, the phenylacetylene can be selectively hydrogenated. Such hydrogenation may be done employing conventional hydrogenation techniques. The hydrogenation may be high pressure or low pressure depending on the catalyst selected. Suitable catalysts include Raney nickel, platinum, palladium, ruthenium, rhodium, copper chromite and the like. The particular mode of hydrogenation will depend primarily on materials and equipment most readily available or economically desirable. The organolithium compounds employed in the practice of the present invention are well known in the art, and are disclosed in the following U.S. Pat. Nos. 3,660,536; 3,663,634; 3,668,263; 3,684,780; 3,725,368; 3,734,973; 3,776,893; 3,776,964; 3,784,637; 3,787,510; 3,954,894; 4,172,100; 4,172,190; 4,182,818; 4,196,153; 4,196,154; 4,200,718; 4,201,729; and 4,205,016, the teachings of which are herewith incorporated by reference thereto.

Generally, for molding and extrusion polystyrene having a weight average molecular weight in the range of about 150,000 to about 300,000 gram moles is desired. The molecular weight is generally readily controlled by using the appropriate quantity of organolithium initiator. It is desirable that the amount of organolithium initiator be maintained at as low a level as possible as residual lithium compounds in polystyrene tend to contribute to a yellow coloration. In order to prepare a polymer in the range of 150,000 to 350,000 weight average molecular weight in a plug flow reactor, between about 300 and 500 parts per million of n-butyllithium would be employed resulting in a polymer having a definite yellowish or amber cast. Employing the present invention using a continuously stirred tank reactor only from 100 to 150 parts per million of n-butyllithium are required, resulting in a polymer that appears to be almost water-white, that is, transparent with no visible coloration.

Reactors suitable for polymerization in accordance with the present invention are the so-called continuously stirred tank reactors. By the term "continuously stirred tank reactor" is meant a reactor in which a stream to be processed is continuously mixed to maintain the composition within the reactor generally constant. Such a tank reactor may have a variety of configurations; for example, a cylindrical reactor having a dished head and bottom which is provided with an agitator capable of circulating the contents of the reactor around the periphery and vertically. Also useful as a continuously stirred tank reactor is the so-called coil reactor which comprises basically a recirculating loop, the loop having a pump therein which circulates the contents of the loop at a rate sufficiently rapid that no significant compositional variation is detected if the loop is sampled at different locations. Suitable reactors are set forth in U.S. Pat. Nos. 2,745,824; 2,989,517; 3,035,033; 3,747,899 and 3,765,655, the teachings of which are herewith incorporated by reference thereto. Such reactors are exemplary of reactors suitable for the practice of the present invention.

The present invention is further illustrated but not limited by the following example.

EXAMPLE

A C$_8$ cut from the distillation of pyrolysis gasoline was analyzed by a gas chromatograph and found to contain 46.96 weight percent xylene, 50.33 weight percent styrene and 0.74 weight percent phenylacetylene. The remaining fraction of the stream was a variety of generally nonreactive C$_8$ compounds. 900 Milliliters of the C$_8$ cut were placed in a 3-liter flask equipped with a magnetic stirrer and a hydrogen inlet and outlet. 30 Grams of a carbon supported palladium catalyst were added to the flask. The flask was then flushed with hydrogen and the contents of the flask were agitated with the magnetic stirrer. The temperature of the reaction mixture was about 25° C. The contents of the flask were analyzed by gas chromatograph at 10 minute intervals to detect the presence of phenylacetylene. After a period of 50 minutes, the gas chromatograph indicated no detectable phenylacetylene. The analysis of the stream at the end of 50 minutes indicated 27.41 weight percent xylene, 50.68 weight percent styrene. The filtered reaction mixture was distilled through a 48-inch by one-inch column under a pressure of 50 millimeters of mercury employing a 3-3 reflux ratio. The first 50 milliliters of distillate were discarded. 200 Milliliters of the distillate were charged to a dry round bottom flask fitted with an agitator and an opening closed by a rubber septum. The distillate was titrated with a 1 n solution of n-butyllithium in cyclohexane until a slight reddish color persisted in the contents of the flask. 1.8 Milliliters of the n-butyllithium solution were required. An additional 1.3 milliliters of the n-butyllithium solution were added. Polymerization of the contents occurred over a period of about 20 minutes and the contents of the flask reached a temperature of 80° C. and the polymer subsequently recovered and devolatilized. Gel permeation chromatograph of the polystyrene obtained a weight average molecular weight of 160,000 gram moles, a normal average molecular weight of 90,000. From the amount of lithium initiator added, the theoretical average molecular weight was 100,000.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A process for the preparation of styrene polymers from a petroleum byproduct stream by providing a byproduct stream from the cracking of petroleum products, the stream containing primarily compounds containing 8 carbons and of an aromatic nature, the stream comprising 30 to 60 parts by weight styrene, 40 to 70 parts by weight of mixed isomers of xylene and 0.5 to 2 parts by weight of phenylacetylene, hydrogenating at least a major portion of the phenylacetylene in the stream to styrene, passing the hydrogenated stream to a continuously stirred tank reactor and initiating polymerization of the styrene in the stream with an organolithium initiator whereby at least 99 percent of the styrene initially present in the stream is converted to polymer, discharging the stream from the reactor and recovering styrene polymer therefrom.

2. The method of claim 1 wherein phenylacetylene is hydrogenated employing a palladium catalyst.

3. The method of claim 1 wherein the organolithium compound is n-butyllithium.

4. The process of claim 1 wherein the reactor has the configuration of a recirculating loop.

* * * * *